United States Patent [19]
Petrov

[11] Patent Number: 6,156,943
[45] Date of Patent: Dec. 5, 2000

[54] HALOGENATED HYDROCARBONS CONTAINING FLUORINE AND PROCESSES FOR THEIR MANUFACTURE

[75] Inventor: Viacheslav Alexandrovich Petrov, Hockessin, Del.

[73] Assignee: E. I. du Pont de Nemours and Company, Wilmington, Del.

[21] Appl. No.: 09/183,079

[22] Filed: Oct. 30, 1998

Related U.S. Application Data

[60] Provisional application No. 60/066,712, Nov. 21, 1997.
[51] Int. Cl.$^7$ ..................................... C07C 19/08
[52] U.S. Cl. .......................... 570/149; 570/132; 570/135; 570/153
[58] Field of Search ................... 570/132, 149, 570/135, 153

[56] References Cited

U.S. PATENT DOCUMENTS

| | | |
|---|---|---|
| 2,427,116 | 9/1947 | Barrick . |
| 2,462,347 | 2/1949 | Barrick . |
| 2,848,504 | 8/1958 | Dixon . |
| 2,957,032 | 10/1960 | Hauptschein . |
| 3,316,312 | 4/1967 | McCane . |
| 3,852,474 | 12/1974 | Simons . |
| 3,954,893 | 5/1976 | O'Neill . |
| 3,996,299 | 12/1976 | Fozzard . |
| 5,162,594 | 11/1992 | Krespan ................................. 570/126 |

OTHER PUBLICATIONS

Krespan et al., *Chem. Rev.*, 96, 3269–3301, 1996.
Snegirev et al., Catalytic and Hydride Reduction of Hexafluoropropylene Dimers, *Plenum Publishing Corporation*, 2489–2494, 1984.

*Primary Examiner*—Alan Siegel

[57] ABSTRACT

Processes are disclosed for producing hydrohaloolefins having the formula $CF_2=C(CH_2RF)CF_3$, the formula $FRCF=C(CH_2RF)CF_3$ or the formula $FRCF=C(CH_2RF)(CF_2RF)$ wherein each R is a difinctional group of the formula $—C_2F_2XY—$ where X and Y are attached to the same carbon, each X is H, Br, Cl or F and each Y is F or $CF_3$. The processes involve reacting $(CF_3)_2C=CH_2$ or certain olefinic adducts thereof with a second olefm of the formula $CF_2=CXY$ in the liquid phase in the presence of a Lewis acid catalyst selected from the group consisting of antimony pentafluoride and aluminum chlorofluoride.

Also disclosed is 1,1,2,2,-tetrafluoro-3,3-bistrifluoromethyl-cyclobutane and a process for its production which involves reacting $(CF_3)_2C=CH_2$ with $CF_2=CF_2$ in the liquid phase in the presence of a Lewis acid catalyst selected from the group consisting of antimony pentafluoride and aluminum chlorofluoride.

Also disclosed are olefins of the formula $FRCF=C(CH_2RF)CF_3$, $FRCF=C(CH_2RF)(CF_2RF)$ or $CF_2=C(CH_2R^1F.)CF_3$ (R, X and Y are defined as above) wherein $R^1$ is $—C_2F_2X(CF_3)—$ where X and $(CF_3)$ are attached to the same carbon or $—C_2F_3X^1—$ wherein $X^1$ is H, Br or Cl.

3 Claims, No Drawings

HALOGENATED HYDROCARBONS CONTAINING FLUORINE AND PROCESSES FOR THEIR MANUFACTURE

This application claims the priority benefit of U.S. Provisional Application Ser. No. 60/066,712, filed Nov. 21, 1997.

FIELD OF THE INVENTION

This invention concerns a processes for the Lewis acid catalyzed condensation of haloolefins with hexafluoroisobutylene (i.e, $(CF_3)_2C=CH_2$ or HFIB) or with olefinic adducts of HFIB and products thereof.

BACKGROUND

Antimony pentafluoride and aluminum chlorofluoride have been reported to catalyze the addition of fluoroalkenes having allylic fluorine atoms to fluoroolefins (see C. G. Krespan and V. A. Petrov, Chem. Rev., 1996, 96(8), 3269–3301, especially, the discussion beginning at page 3274, and U.S. Pat. No. 5,162,594).

The olefinic adduct products of these reactions are useful as solvents and stable liquids, particularly, after the double bond has been saturated by, for example, hydrogenation or fluorination. The adduct products may also be useful as monomers for the preparation of fluoropolymers. There is an interest in developing more efficient processes for the manufacture of fluoroolefins and also hydrofluoroolefins.

SUMMARY OF THE INVENTION

A process is provided for producing a hydrohaloolefin from the group consisting of $CF_2=C(CH_2RF)CF_3$, $FRCF=C(CH_2RF)CF_3$ and $FRCF=C(CH_2RF)(CF_2RF)$ wherein each R is a difunctional group of the formula —$C_2F_2XY$— where X and Y are attached to the same carbon, wherein X is selected from the group consisting of H, Br, Cl and F and wherein Y is selected from the group consisting of F and $CF_3$. This process comprises reacting the olefin $(CF_3)_2C=CH_2$ with a second olefin of the formula $CF_2=CXY$ in the liquid phase in the presence of a Lewis acid catalyst selected from the group consisting of antimony pentafluoride and aluminum chlorofluoride.

Also provided is a process for producing a hydrohaloolefin from the group consisting of $FRCF=C(CH_2CF_2CXYF)CF_3$, $FRCF=C(CH_2CXYCF_3)CF_3$, $FRCF=C(CH_2CF_2CXYF)CF_2RF$ and $FRCF=C(CH_2CXYCF_3)CF_2RF$ wherein R, X and Y are as defined above. This process comprises reacting the corresponding olefin (with regard to X and Y position) selected from $CF_2=C(CH_2CF_2CXYF)CF_3$ and $CF_2=C(CH_2CXYCF_3)CF_3$ with a second olefin of the formula $CF_2=CXY$ in the liquid phase in the presence of a Lewis acid catalyst selected from the group consisting of antimony pentafluoride and aluminum chlorofluoride.

Also provided is a process for producing a hydrohaloolefin from the group consisting of $CXYFCF_2CF=C(CH_2CF_2CXYF)CF_2RF$, $CF_3CXYCF=C(CH_2CF_2CXYF)CF_2RF$, $CXYFCF_2CF=C(CH_2CXYCF_3)CF_2RF$ and $CF_3CXYCF=C(CH_2CXYCF_3)CF_2RF$, wherein R, X and Y are as defined above. This process comprises reacting the corresponding olefin (with regard to X and Y position) selected from $CXYFCF_2CF=C(CH_2CF_2CXYF)CF_3$, $CF_3CXYCF=C(CH_2CF_2CXYF)CF_3$, $CXYFCF_2CF=C(CH_2CXYCF_3)CF_3$ and $CF_3CXYCF=C(CH_2CXYCF_3)CF_3$ with a second olefin of the formula $CF_2=CXY$ in the liquid phase in the presence of a Lewis acid catalyst selected from the group consisting of antimony pentafluoride and aluminum chlorofluoride.

A process for producing 1,1,2,2-tetrafluoro-3,3-bis-trifluoromethyl-cyclobutane is also provided. This process comprises reacting $(CF_3)_2C=CH_2$ with $CF_2=CF_2$ in the liquid phase in the presence of a Lewis acid catalyst selected from the group consisting of antimony pentafluoride and aluminum chlorofluoride.

Also provided are olefins selected from the group consisting of $FRCF=C(CH_2RF)CF_3$, $FRCF=C(CH_2RF)(CF_2RF)$ and $CF_2=C(CH_2R^1F)CF_3$ wherein R, X and Y are defined as above, and $R^1$ is a difunctional group selected from the group consisting of (i) —$C_2F_2X(CF_3)$— where X and ($CF_3$) are attached to the same carbon and (ii) —$C_2F_3X^1$— wherein $X^1$ is selected from the group consisting of H, Br and Cl. The cyclobutane 1,1,2,2-tetrafluoro-3,3-bis-trifluoromethylcyclobutane is also provided.

DETAILED DESCRIPTION OF THE INVENTION

HFIB and olefins of the formula $CF_2=CXY$ can either be obtained commercially or prepared by known art methods. The HFIB olefinic adducts can be prepared by the Lewis acid catalyzed addition of the olefins shown to HFIB using the process of this invention. For example, $CF_2=C(CF_3)CH_2C_2F_5$ can be prepared by the Lewis acid catalyzed addition of $CF_2=CF_2$ to $(CF_3)_2C=CH_2$; $C_2F_5CF=C(CF_3)CH_2C_2F_5$ can be prepared by the Lewis acid catalyzed addition of $CF_2=CF_2$ to $CF_2=C(CF_3)CH_2C_2F_5$; $CF_2=C(CF_3)CH_2CF(CF_3)_2$ can be prepared by the Lewis acid catalyzed addition of $CF_2=CFCF_3$ to $(CF_3)_2C=CH_2$; $CF_2=C(CF_3)CH_2CH(CF_3)_2$ can be prepared by the Lewis acid catalyzed addition of $CF_2=CHCF_3$ to $(CF_3)_2C=CH_2$; $CF_2=C(CF_3)CH_2CHFCF_3$ can be prepared by the Lewis acid catalyzed addition of $CF_2=CHF$ to $(CF_3)_2C=CH_2$; and both $CF_2=C(CF_3)CH_2CClFCF_3$ and $CF_2=C(CF_3)CH_2CF_2CClF_2$ can be prepared by 35 the Lewis acid catalyzed addition of $CF_2=CClF$ to $(CF_3)_2C=CH_2$.

Solvents or diluents may be employed in the process of the present invention. The solvent or diluent is selected so that it will not be reactive in the process or lead to the deactivation of the antimony fluoride catalyst. Suitable solvents or diluents may be selected from the group consisting of perfluoroalkanes or perfluoroethers (e.g., perfluorocyclobutane); the cyclic dimer of hexafluoropropene (i.e., the isomeric perfluorodimethylcyclobutanes); perfluoroethers or perfluoro tertiary amines. Preferred on the basis of its ready availability to those skilled in the art is the cyclic dimer of hexafluoropropene.

The process of this invention is catalyzed by Lewis acids such as $SbF_5$ and $AlZ_3$, where Z is one or more of Br, F or Cl, provided that Z cannot be entirely F. Preferred catalysts are $SbF_5$ and $AlCl_xF_y$ (mixed aluminum halide), where the total number of atoms of halide, x plus y equals 3, where x ranges from about 0.05 to 2.95 and y ranges from about 2.95 to 0.05. Details of the aluminum chlorofluoride catalyst preparation are disclosed in U.S. Pat. No. 5,162,594 which is incorporated herein by reference.

The temperature employed in the process of the present invention typically ranges from about −10° C. to about 100° C. The preferred temperature range is from about 0° C. to 80° C.

Reaction time is not critical and typically ranges from about 5 seconds to about 24 hours. From about 1 to 12 hours, are usually sufficient.

The pressure employed in the reaction is not critical. The reaction is normally run at pressures in the range of from 0 to 300 psig (101 kPa to 2169 kPa). Autogenous pressures are usually employed; however the pressure should not be allowed to rise above 300 psig when using tetrafluoroethylene because of safety considerations.

Where the reaction conditions are heterogeneous, some degree of agitation is often desirable.

Since the catalysts are water sensitive, reagents and equipment should be dried before use.

Of note are reactions wherein each X is F. Examples of the olefin $CF_2=CXY$ include $CF_2=CHF$, $CF_2=CHCF_3$, $CF_2=CBrF$, $CF_2=CBrCF_3$, $CF_2=CClF$, $CF_2=CClCF_3$, $CF_2=CF_2$, and $CF_2=CFCF_3$.

The proportion of the first olefin, namely, $(CF_3)_2C=CH_2$, $CF_2=C(CH_2RF)CF_3$, or $FRCF=C(CH_2RF)CF_3$ to the second olefin, namely, $CF_2=CXY$, wherein R, X and Y are the same as defined above, is preferably at least about 1:0.5. As the ratio of the second olefin is increased di-adducts and tri-adducts, in addition to mono-adducts, are formed. For example, when $(CF_3)_2C=CH_2$ and $CF_2=CF_2$ in a molar ratio of 1:2 are reacted in the presence of Lewis acid catalysts according to the process of this invention the following adducts can be isolated; $CF_2=C(CF_3)CH_2C_2F_5$ (mono), $C_2F_5CF=C(CF_3)CH_2C_2F_5$ (di) and $C_2F_5CF=C(C_3F_7)CH_2C_2F_5$ (tri).

The proportion of catalyst to the first olefin reactant is typically from about 0.5 weight % to about 15 weight %; and a range of from about 1 weight % to about 10 weight % is generally preferred.

The reaction can be done in batch, semi-batch, semi-continuous or continuous modes in one or more reaction vessels. On a laboratory scale, the reaction can be done in shaker tubes, where all reagents are combined before the reaction vessel is sealed and the reaction begun. It can also be done in autoclaves equipped with an agitator. Product(s) may be isolated by standard chemical engineering techniques, e.g., fractional distillation.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

Table 1 contains a summary of the major products of Examples 1 to 6. Additionally, the major products of Examples 7 to 11, which were run in a similar manner to Examples 1 to 6, are also shown. Table 2 contains a summary of some of the analytical data obtained for the product adducts shown.

EXAMPLE 1

Reaction of HFIB with Tetrafluoroethylene (ratio 1:1)

Hexafluoroisobutene (i.e., $(CF_3)_2C=CH_2$ or HFIB; 82 g, 0.5 mol), $SbF_5$ (30 g, 0.14 mol) and tetrafluoroethylene (50 g, 0.5 mol) were charged into a 400 mL Hastelloy™ nickel alloy reactor and agitated at 25° C. for 12 hours. The reaction mixture was poured onto ice, the organic (lower) layer was separated and dried over $P_2O_5$. Fractionation of the liquid product gave 75 g (73% yield) of a fraction, b.p. 64–67° C., containing 95% $CF_2=C(CF_3)CH_2C_2F_5$ and 5%

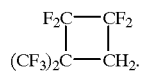

EXAMPLE 2

Reaction of HFIB with Tetrafluoroethylene (ratio 1:2)

Hexafluoroisobutene (HFIB) (41 g, 0.25 mol), $SbF_5$ (10 g, 0.046 mol) and tetrafluoroethylene (50 g, 0.5 mol) were charged into a 400 mL Hastelloy™ nickel alloy reactor and agitated at 25° C. for 12 hours. The reaction mixture was poured onto ice, the organic (lower) layer (85 g) was separated and dried over $P_2O_5$ and analyzed by GC. The crude product was a mixture of 4% HFIB, 20% monoadduct (formulas A and A1 shown below, ratio HFIB/TFE 1:1), 65% diadduct (formula B shown below, HFIB/TFE 1:2) and 9% triadduct (formula C shown below, HFIB/TFE 1:3). Fractionation of the crude material using a spinning-band distillation column afforded a mixture (5 g) containing $CF_2=C(CF_3)CH_2C_2F_5$ (A) and

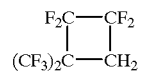

(A1) b.p. 62–65° C.; 38 g of $C_2F_5CH_2C(CF_3)=CFC_2F_5$, (B) b.p. 97–100° C. (mixture of E and Z isomers, ratio 95:5, see Table 1), and 6 g of $C_2F_5CH_2C(n-C_3F_7)=CFC_2F_5$, (C) mixture of E and Z isomers (ratio 58:42), b.p. 125–126.5° C.; IR 1695 cm$^{-1}$ (C=C).

EXAMPLE 3

Reaction of HFIB with Trifluoroethylene

Hexafluoroisobutene (HFIB) (82 g, 0.5 mol), $SbF_5$ (20 g, 0.092 mol) and trifluoroethylene (40 g, 0.5 mol) were charged into a 400 mL Hastelloy™ nickel alloy reactor and agitated at 25° C. for 12 hours. The reaction mixture was poured on ice, the organic (lower) layer was separated and dried over $P_2O_5$. The crude product was a mixture of 29% of HFIB, 14% $CF_2=C(CF_3)CH_2CHFCF_3$ and 57% of a mixture of stereoisomers of $CF_3CHFC(CF_3)=CFCHFCF_3$. Fractionation of the liquid product gave 30 g (37% yield) of a fraction, b.p. 106–111° C. (see Table 1).

EXAMPLE 4

Reaction of $(CF_3)_2CFCH_2C(CF_3)=CF_2$ with TFE $(CF_3)_2CFCH_2C(CF_3)=CF_2$ (62 g, 0.2 mol), $SbF_5$ (20 g, 0.092 mol) and TFE (20 g, 0.2 mol) were charged into a 400 mL Hastelloy™ nickel alloy reactor and agitated at 25° C. for 12 hours. The reaction mixture was poured onto ice, the organic (lower) layer was separated and dried over $P_2O_5$. The crude product (78 g) was distilled to give 50 g of material, b.p. 116–1180C, which was a mixture of E and Z isomers of $(CF_3)_2CFCH_2C(CF_3)=CFC_2F_5$ in a ratio of 89:11 (see Table 1).

EXAMPLE 5

Reaction of HFIB and Hexafluoropropene (HFP) Catalyzed by Aluminum Chlorofluoride Hexafluoroisobutene (HFIB) (32 g, 0.2 mol), aluminum chlorofluoride $AlCl_xF_y$ (5 g) and hexafluoropropene (30 g, 0.2 mol) were charged into a 400 mL Hastelloy™ nickel alloy reactor and agitated at 50° C. for 12 hours. The reaction mixture was poured onto ice, the organic (lower) layer was separated, dried over $P_2O_5$ and distilled to give 21 g (34% yield) of $(CF_3)_2CFCH_2C(CF_3)=CF_2$, b.p. 80.5–81.5 (see Table 1).

EXAMPLE 6

Reaction of HFIB and TFE Catalyzed by Aluminum Chlorofluoride

Hexafluoroisobutene (HFIB) (60 g, 0.36 mol), aluminum chlorofluoride $AlCl_xF_y$ (5 g) and TFE (25 g, 0.25 mol) were charged into a 400 mL Hastelloy™ nickel alloy reactor and agitated at 25° C. for 12 hours. The reaction mixture was poured onto ice, the organic (lower) layer was separated and dried over $P_2O_5$ The crude product (55 g) was distilled to give 35 g of an 90:10 mixture of $CF_2=C(CF_3)CH_2C_2F_5$ and

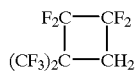

b.p. 62–65° C. The yield of the olefin was 42%.

TABLE 1

Reaction of $CF_2=CF_2$(TFE), $CF_2=CFCF_3$(HFP), $CHF=CF_2$(TrFE), $(CF_3)_2C=CH_2$(HFIB), $CF_2=C(CF_3)CH_2C_2F_5$(HFIB-E) or $CF_2=C(CF_3)CH_2CF(CF_3)_2$(HFIB-P) with Fluoroolefins Catalyzed by Lewis Acids

| Ex. No. | Reactants (mol) | Cat. (g) | T(° C.) Time (hrs). | Products (% yield[a]) |
|---|---|---|---|---|
| 1 | HFIB (0.5) TFE (0.5) | SbF$_5$ (30) | 25 (12) | $CF_2=C(CF_3)CH_2C_2F_5$[b] (73) |
| 2 | HFIB (0.25) TFE (0.5) | SbF$_5$ (10) | 25 (12) | $C_2F_5CF=C(CF_3)CH_2C_2F_5$ (61) |
| 3 | HFIB (0.5) TrFE[d] (0.5) | SbF$_5$ (20) | 25 (12) | $CF_2=C(CF_3)CH_2CHFCF_3$ (11)[c] $CF_3CHFCF=C(CF_3)CH_2CHFCF_3$ (37) |
| 4 | HFIB-P (0.2) TFE (0.2) | SbF$_5$ (20) | 25 (12) | $C_2F_5CF=C(CF_3)CH_2CF(CF_3)_2$ (62) |
| 5 | HFIB (0.2) HFP (0.2) | ACF (5) | 50 (12) | $CF_2=C(CF_3)CH_2CF(CF_3)_2$ (34) |
| 6 | HFIB (0.5) TFE (0.5) | ACF[e] (5) | 25 (12) | $CF_2=C(CF_3)CH_2C_2F_5$[b] (39)[f] |
| 7 | HFIB (0.53) HFP (0.47) | SbF$_5$ (15) | 80 (16) | $(CF_3)_2CFCF=C(CF_3)CH_2CF(CF_3)_2$[g] (5) |
| 8 | HFIB (0.5) $CF_2=CHCF_3$ (0.5) | SbF$_5$ (20) | 25 (12) | $CF_2=C(CF_3)CH_2CH(CF_3)_2$[h] (56)[c] |
| 9 | HFIB (0.5) HFP (0.5) | SbF$_5$ (20) | 50 (12) | $CF_2=C(CF_3)CH_2CF(CF_3)_2$ (56) |
| 10 | HFIB-P (0.37) TrFE (0.2) | SbF$_5$ (20) | 25 (12) | $CF_3CHFCF=C(CF_3)CH_2CF(CF_3)_2$ (33) |
| 11 | HFIB-E (0.28) TrFE (0.9) | SbF$_5$ (20) | 25 (12) | $CF_3CHFCF=C(CF_3)CH_2CF_2CF_3$ (42) |

[a]isolated yield
[b]isolated product contained 5 to 10% of 2,2-H-F-1,1-dimethylcyclobutane
[c]calculated yield
[d]trifluoroethylene
[e]aluminum chlorofluoride $AlCl_xF_y$
[f]conversion of HFIB 72%
[g]isolated by preparative GC
[h]crude product contained 35% $CF_3CH=CFCH(CF_3)_2$ and 65% $CF_2=C(CF_3)CH_2CH(CF_3)_2$; sample of pure product was isolated by distillation

TABLE 2

Analytical Data for the Preparation of $R'_fCF=C(CF_3)CH_2R_f$ by Reaction of Hexafluoroisobutene (HFIB) with Fluoroolefins

| Entry No. | $R_f$ | $R'_f$ | b.p. (° C.) | IR (C= C) | Anal. or MS found (calc.) |
|---|---|---|---|---|---|
| 1 | $C_2F_5$— | F— | 64–67[a] | 1749 | m/e 363.9943 (363.9933) |
| 2 | $(CF_3)_2CF$— | F— | 80.5–81.5 | 1747 | C, 26.75 (26.77; H, 0.60 (0.64); F, 72.57 (72.59) |
| 3 | $(CF_3)_2CH$— | F— | 83–83.5 | 1753 | C, 28.64 (28.40), H, 1.26 (1.02); F, 70.34 (70.58) |
| 4 | $CF_3CHF$— | F— | — | 1752 | — |
| 5 | $(CF_3)_2CF$— | $C_2F_5$— | 116–121[b] | 1690 | C, 26.35 (26.11); H, 0.61 (0.49); F, 72.97 (73.41) |
| 6 | $CF_3CHF$— | $CF_3CHF$— | 106–111[c] | 1720 1740 | C, 29.36 (29.29); H, 1.46 (1.43); F, 69.21 (69.48) |
| 7 | $C_2F_5$— | $CF_3CHF$— | 93–95[d] | 1702, 1719 | C, 27.42 (27.76); H, 0.96 (0.87); F, 71.92 (71.36) |
| 8 | $(CF_3)_2CF$— | $CF_3CHF$— | 119[e] | 1698 | C, 27.21 (27.29); H, 0.81 (0.76); F, 71.92 (71.95) |
| 9 | $C_2F_5$— | $C_2F_5$— | 97–100[f] | 1687 | C, 26.19 (26.39); H, 0.39 (0.55); F, 73.06 (73.05) |
| 10 | $(CF_3)_2CF$— | $(CF_3)_2CF$— | g | 1688 | m/e 463.9812 (463.9869) |

[a]compound has 5% of 2,2-H-F-1,1-dimethylcyclobutane
[b]mixture of isomers, E:Z = 89:11
[c]mixture of stereoisomers
[d]mixture of isomers, E:Z = 59:41
[e]mixture of isomers, E:Z = 92:8
[f]mixture of E:Z isomers
[g]isolated by preparative GC

What is claimed is:

1. A process for producing a hydrohaloolefin from the group consisting of $CF_2=C(CH_2RF)CF_3$, $FRCF=C(CH_2RF)CF_3$ and $FRCF=C(CH_2RF)(CF_2RF)$ wherein each R is a difunctional group of the formula —$C_2F_2XY$— where X and Y are attached to the same carbon, wherein X is selected from the group consisting of H, Br, Cl and F and wherein Y is selected from the group consisting of F and $CF_3$, comprising:

reacting the olefin $(CF_3)_2C=CH_2$ with a second olefin of the formula $CF_2=CXY$ in the liquid phase in the presence of a Lewis acid catalyst selected from the group consisting of antimony pentafluoride and aluminum chlorofluoride.

2. The process of claim 1 wherein each X is F.

3. A process for producing 1,1,2,2,-tetrafluoro-3,3-bistrifluoromethyl-cyclobutane, comprising:

reacting $(CF_3)_2C=CH_2$ with $CF_2=CF_2$ in the liquid phase in the presence of a Lewis acid catalyst selected from the group consisting of antimony pentafluoride and aluminum chlorofluoride.

* * * * *